United States Patent
Lehmann et al.

(10) Patent No.: US 6,936,642 B2
(45) Date of Patent: Aug. 30, 2005

(54) DENTAL MATERIALS

(75) Inventors: Thomas Lehmann, Burghausen (DE); Wolfgang Soglowek, Diessen-Obermühlhausen (DE); Reinhold Hecht, Inning-Buch (DE)

(73) Assignee: 3M Espe AG, Seefeld (DE)

( * ) Notice: Subject to any disclaimer, the term of this patent is extended or adjusted under 35 U.S.C. 154(b) by 304 days.

(21) Appl. No.: 10/168,092

(22) PCT Filed: Dec. 15, 2000

(86) PCT No.: PCT/EP00/12774

§ 371 (c)(1), (2), (4) Date: Oct. 3, 2002

(87) PCT Pub. No.: WO01/43700

PCT Pub. Date: Jun. 21, 2001

(65) Prior Publication Data

US 2003/0134932 A1 Jul. 17, 2003

(30) Foreign Application Priority Data

Dec. 17, 1999 (DE) .......................... 199 61 341

(51) Int. Cl.⁷ ............................. A61K 6/08; C08L 75/04
(52) U.S. Cl. ........................ 523/115; 523/116; 106/35; 524/589; 526/301
(58) Field of Search ................................ 523/115, 116; 106/35; 524/589; 526/301

(56) References Cited

U.S. PATENT DOCUMENTS 5,502,087 A  3/1996 Tateosian et al.
6,426,373 B1 * 7/2002 Stange et al. ............... 523/116

FOREIGN PATENT DOCUMENTS

| DE | 37 03 080 A1 | 1/1988 |
| DE | 40 18 183 A1 | 12/1991 |
| DE | 198 41 205 A1 | 3/1999 |
| DE | 198 03 979 A1 | 8/1999 |
| EP | 0 630 640 A1 | 12/1994 |
| EP | 0 231 805 A2 | 8/1997 |
| WO | 96/15179 A2 | 5/1996 |
| WO | 99/40884 A1 | 8/1999 |

OTHER PUBLICATIONS

Marxkors et al., Basiswerkstoffe, Die totale Prothese, pp. 115–116.

* cited by examiner

Primary Examiner—Tae H. Yoon
(74) Attorney, Agent, or Firm—Birch, Stewart, Kolasch & Birch, LLP

(57) ABSTRACT

The invention relates to compositions containing:
(a) 14 to 55 wt.-% fillers,
(b) 3 to 35 wt.-% of at least one mono- or polyethylenically unsaturated compound which is not a urethane (meth)acrylate,
(c) 0.1 to 5 wt.-% of at least one initiator system which is capable of starting a radical reaction,
(d) 1 to 40 wt.-% plasticizers,
(e) 0 to 10 wt.-% auxiliaries such as dyes, pigments, stabilizers, solvents, rheological additives such as flow-improvers and/or retarders, and
(f) 30 to 81.9 wt.-% of at least two urethane (meth)acrylates with different molecular weights, these being present in a molecular weight ratio of 1.5:1 to 50:1.

21 Claims, 1 Drawing Sheet

4-point bending test

DENTAL MATERIALS

Figure 1:
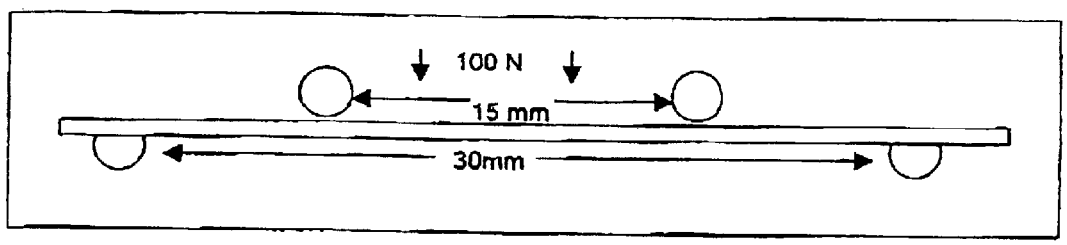

This application is the national phase under 35 U.S.C. § 371 of PCT International Application No. PCT/EPOO/12774 which has an International filing date of Dec. 15, 2000, which designated the United States of America.

The present invention relates to compositions for the preparation of dental materials with improved mechanical properties and the use of such dental materials, in particular as provisional or temporary crowns, bridges, fillings, inlays and onlays.

In the case of the preparation of provisional or temporary crowns, bridges, inlays and onlays, low-viscosity to viscoplastic materials based on ethylenically unsaturated compounds are involved, depending on the use, which can be provided with organic and/or inorganic fillers and cured by polymerization (called "provisional K+B materials" hereafter).

Two different classes of provisional K+B materials are current: on the one hand so-called polymethyl methacrylate materials (PMMA materials) and on the other hand so-called composite materials.

The PMMA materials consist of a powder/liquid system the powder essentially being a PMMA powder with dyes and initiator constituents and the liquid consisting mainly of methyl methacrylate and/or iso-butyl methacrylate and also initiators and stabilizers.

Crowns and bridges prepared from PMMA material are characterized by a low fracture susceptibility and good elastic properties. A decided disadvantage of these materials is however that they are irreversibly deformed if a load is placed on them.

Thus with PMMA materials, material is provided which is less fracture prone, but however easily permanently deformable, which becomes unusable for the patient if too great a load is placed on it. In addition materials based on PMMA are physiologically questionable as they contain toxic acrylate systems.

The composite materials normally consist of paste/paste systems which can be either manually admixed or present in a double-chambered cartridge and are admixed by means of a dispenser and a static mixing device, as described in EP-A-0 232 733 and EP-A-0 261 466. In the case of the monomers used in this material class, mainly difunctional ethylenically unsaturated compounds are involved which, when curing, effect a high cross-linking level of the resulting polymer matrix. Glass powder, silica gels and quartzes are essentially used as fillers.

Through the high cross-linking level and the hard fillers, hard and brittle materials are obtained which do not flow under a great load, but fracture.

With composite materials therefore, a material is provided which is very dimensionally stable, but however fracture prone, which likewise becomes unusable for the patient if too great a load is placed on it.

From the state of the art, urethane (meth)acrylates, essentially 7,7,9-trimethyl-4,13-dioxo-3,14-dioxa-5,12-diazahexadecane-1,16-dioxy-dimethacrylate (UDMA, for example Plex 666-1, Röhm, Darmstadt) have also been described as monomers for composite materials.

By acrylates or (meth)acrylates are meant in general acrylates and/or methacrylates within the framework of this document.

UDMA slightly improves the fracture susceptibility, however composites prepared with UDMA are still always brittle materials which are fracture prone in particular in thin areas or when used in bridges.

In order to further reduce fracture susceptibility, different unsuccessful attempts have been carried out:

The incorporation of polymers which, due to the marked swelling behaviour in the monomer matrix, leads to a marked increase in viscosity.

The use of plasticizers which is accompanied by a marked decline in mechanical properties such as the compression and bending strength as well as the release of harmful substances into bodily fluids.

The use of high-molecular, low-functional monomers, such as polyethylene glycol diacrylate which improves the fracture susceptibility, but greatly reduces the mechanical properties and also leads to a marked increase in temperature during curing and is therefore not usable for application in the mouth.

In summary, none of the methods known to date leads to a usable improvement of the fracture susceptibility and dimensional stability of provisional composite-based K+B materials.

DE 198 41 205 A describes light-curing resin materials for orthodontics which, in addition to fillers, initiator systems and plasticizers, contain (meth)acrylates containing urethane bonds with a molecular weight of 300 to 5,000 g/mol and at least one unsaturated double bond, mixtures of such compounds of different molecular weight not being ruled out, as well as in addition (meth)acrylates free of urethane bonds with an average molecular weight of 100 to 300 g/mol and at least one unsaturated double bond. In relation to the previously named compounds, it is stated in the description in lines 12 to 14 of page 3, that the molecular weight may not exceed 300 as otherwise the obtained cured material is brittle and is unsuitably defective in terms of durability.

WO 99/40884 describes dental materials based on polymerizable acrylic monomers, polymerization initiators and inhibitors as well as fillers. Compositions which contain urethane (meth)acrylates with different molecular weights as well as unsaturated compounds which have no urethane (meth)acrylate, are not disclosed here. The compositions described in the examples contain an single urethane methacrylate.

The object of the invention is to provide a composite-based dental material which has a reduced fracture susceptibility with simultaneously high dimensional stability.

This object is achieved by compositions containing:
(a) 14 to 60 wt.-%, preferably 20 to 50 wt.-% fillers,
(b) 3 to 35 wt.-%, preferably 5 to 25 wt.-% of at least one mono- or polyethylenically unsaturated compound which is not a urethane (meth)acrylate, and has a molecular weight between 300 and 5,000 g/mol,
(c) 0.1 to 5 wt.-%, preferably 0.1 to 4 wt.-% of at least one initiator system which is capable of starting a radical reaction,
(d) 1 to 40 wt.-%, preferably 2 to 30 wt.-% plasticizers,
(e) 0 to 10 wt.-%, preferably 0.000001 to 8 wt.-% auxiliaries such as dyes, pigments, stabilizers, solvents, rheological additives such as flow-improvers and/or retarders, and
(f) 30 to 81.9 wt.-%, preferably 35 to 73 wt.-% of at least two urethane (meth)acrylates with different molecular weights, these being present in a molecular weight ratio of 1.5:1 to 50:1 and the higher molecular urethane (meth)acrylate having a molecular weight between 1,000 and 20,000 g/mol and the lower molecular urethane (meth)acrylate a molecular weight between 300 and 1,000 g/mol.

The materials according to the invention are suitable in particular for use in the preparation of provisional or temporary crowns, bridges, fillings, inlays and onlays.

It was surprisingly found that materials prepared from the compositions according to the invention display a much-improved fracture susceptibility with simultaneously high dimensional stability. The materials according to the invention have improved elastic properties with extensive retention of mechanical stability.

The terms "comprising" or "containing" are always intended to introduce a non-limitative list within the framework of this document.

The fact that the word "a" is used before naming a feature does not exclude the possibility that the named features can be present many times, in the sense of "at least one".

Component (a) comprises customary fillers for dental materials, for example glass and quartz powder, silica gels, pyrogenic highly-dispersed silicic acids, insoluble plastics, low soluble fluorides, as described in U.S. Pat. No. 5,824,720, as well as mixtures of these components. These fillers can be X-ray opaque through suitable additives, such as for example barium or strontium-containing glasses or also through compounds such as $YF_3$. Pyrogenic highly-dispersed silicic acids are suitable for example as fillers influencing thixotropy. Furthermore soluble organic polymerisates, such as polyvinyl acetate as well as its copolymers can also be added in such a quantity that the viscosity of the pastes allows them to be used in cartridge systems customary in the trade, as described in EP-A-0 232 733 and EP-A-0 261 466.

Cristobalite, calcium silicate, zirconium silicate, molecular sieves such as sodium aluminium silicate, metal oxide powder such as aluminium or zinc oxide or their mixed oxides, barium sulphate, yttrium fluoride, calcium carbonate, plaster and plastic powder are for example also suitable as fillers.

The named fillers can be hydrophobized for example by a treatment with organosilanes or -siloxanes or by the etherification of hydroxyl groups to alkoxy groups.

It has been shown that the use of purely organic, insoluble fillers is not suitable to achieve the present object, as aesthetically low-grade dental materials with unsatisfactory physical values are obtained.

Component (b) is an at least mono- or polyethylenically unsaturated compound which is not a urethane (meth)acrylate and preferably has a viscosity smaller than 5 Pa·s at 23° C. (cone/plate viscometer). Compounds with a different viscosity are also suitable however. The compounds have a molecular weight between 300 g/mol and 5,000 g/mol, particularly preferably between 300 g/mol and 1,000 g/mol.

Acrylic acid esters and/or methacrylic acid esters of an ethoxylated and/or propoxylated compound, of a polyether or of an alkylpolyol are particularly suitable as component (b).

This can involve for example Di(meth)acrylates of alkyl compounds, preferably with 2 to 20 C atoms. Di(meth)acrylates of hexanediol (6 C atoms), octanediol (8 C atoms), nonanediol (9 C atoms), decanediol (10 C atoms) and eicosanediol (20 C atoms) are preferred.

Di(meth)acrylates of ethoxylated and/or propoxylated compounds, for example of ethylene glycol, polyethylene glycols, polypropylene glycols, polyethylene-co-propylene glycols are also suitable.

Furthermore Di(meth)acrylates of ethoxylated Bisphenol A, for example 2,2'-bis (4-(meth)acryloxy-tetraethoxyphenyl)propane are suitable.

As component (c), the compositions according to the invention contain at least one initiator system which is suitable for generating radicals. Redox systems or radiation-curing systems or also mixtures of different catalyst systems are principally suitable.

For example, an initiator system consisting of an amine and a peroxide component as described in DT-PS-97 50 72, can be a redox system. The polymerization is started here by the peroxide compound. A tertiary amine is used for example as polymerization accelerator. A further suitable system is also described by Albert Groβ in "Quintessenz der Zahntechnik [Essentials of Dentistry]", 1977, 7, Report No. 293. Usually, the amine component is worked into a paste, the so-called base paste. For the most part, this base paste also contains the monomers provided for polymerization. The peroxide component is worked into another paste, the so-called catalyst paste. The spatial separation of the two initiator components is necessary to avoid a premature curing of the monomer proportions.

A similar initiator system for the polymerization of unsaturated hydrocarbons is also described in DE-A-95 56 33, which contains heavy metals and also an amine and sulfonium component. Also named in EP-A-0 374 824 is an initiator system with an organic peroxide compound and a tertiary aromatic amine as activator (accelerator). For example, all these systems can be used alone or in combination in the compositions according to the invention.

The initiator systems have a more favourable temperature development and also an improved colour stability which is described for example in DT-C-14 95 520. The composition from DT-C-14 95 520 polymerizes at low temperature in a short time and without using external energy. The described systems contain barbituric acid derivatives and/or malonylsulfamides, ionogenically-bonded halogen and/or a heavy metal compound and/or organic peroxides. EP-A-0 374 824 also describes such an initiator system of barbituric acid derivative, peroxide, heavy metal compound and ionogenic halogen.

Furthermore the polymerizable composition according to the invention can contain a photoinitiator system. This can also be present in addition to at least one of the other initiator systems or as a single initiator system. Suitable photoinitiators are for example the bisacylphosphine oxides described in U.S. Pat. No. 4,792,632 and U.S. Pat. No. 4,737,593.

It is essential for the invention that the initiator systems require no supply of energy in the form of heat to produce radicals. Heat-curing systems are unusable for use as dental materials, in particular materials which cure in the patient's mouth.

The polymerizable compositions according to the invention can contain customary plasticizers, preferably with a viscosity smaller than 10 Pa·s at 23° C. (cone/plate viscometer), as component (d). These are for example polyethylene glycol derivatives, polypropylene glycols, low-molecular polyesters, dibutyl, dioctyl, dinonyl, diphenyl phthalate, di(iso-nonyladipate), tricresyl phosphate, paraffin oils and silicone oils.

Auxiliaries, such as dyes, pigments, stabilizers, solvents and/or rheological additives such as flow-improvers can be added as component (e).

Furthermore the vinyl compounds described in EP-A-0 374 824 as component (d) can be used for example as retarders to lengthen the setting times.

Component (f) consists of at least two urethane (meth)acrylates with different molecular weights with a molecular weight ratio of 1.5:1 to 50:1, preferably 1.5:1 to 20:1, particularly preferably 1.5:1 to 10:1 and quite particularly preferably 1.5:1 to 5:1. It is particularly advantageous if, in the compositions according to the invention, the acrylates of this component constitute at least 50 wt.-%, preferably at least 60 wt.-%, particularly preferably at least 70 wt.-% of the total ethylenically unsaturated compounds [(b)+(f)].

The higher molecular acrylates of this component have a molecular weight between 1,000 g/mol and 20,000 g/mol, preferably between 1,000 g/mol and 15,000 g/mol and particularly preferably between 1,000 g/mol and 10,000 g/mol.

The lower molecular acrylates of this component have a molecular weight between 300 g/mol and 1,000 g/mol.

The higher-molecular urethane (meth)acrylate of component (f) can be a polyester, polyether, polybutadiene and/or polycarbonate urethane oligomer (meth)acrylate.

By polyether urethane oligomer (meth)acrylate is meant a compound for example which contains at least polyether, urethane and (meth)acrylate groupings.

These urethane oligomer (meth)acrylates are accessible, in that a polyester, polyether, polybutadiene and/or polycarbonate diol (diol component) with an aliphatic, cycloaliphatic and/or aromatic diisocyanate, for example 1,6-hexamethylene diisocyanate (HDI), 2,4,4-trimethylhexamethylene-1,6-diisocyanate (TMDI), tetramethylene diisocyanate, isophoron diisocyanate, 4,4'-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate (diisocyanate component) are reacted under amine or tin catalysis (C. Hepburn, "Polyurethane Elastomers", $2^{nd}$ Ed. Elsevier Applied Science, London and New York, 1992). If a molar excess of diol component compared with diisocyanate component is hereby used, terminal OH groups remain which can be esterified with an ethylenically unsaturated acid such as acrylic acid or methacrylic acid or one of their derivatives. If a molar excess of diisocyanate component compared with diol component is used, terminal isocyanate groups remain which are reacted with a hydroxyalkyl and/or hydroxyaryl (meth)acrylate and/or di(meth)acrylate and/or tri(meth)acrylate, such as for example 2-hydroxyethyl acrylate (HEA), 2-hydroxyethyl methacrylate (HEMA), 3-hydroxypropyl methacrylate (HPMA), 3-hydroxypropyl acrylate (HPA), glycerol dimethacrylate and/or glycerol diacrylate.

The preparation of the previously named urethane (meth) acrylates can be inferred from C. Hepburn, "Polyurethane Elastomers", $2^{nd}$ Ed. Elsevier Applied Science, London and New York, 1992.

Usable polycarbonate polyols are for example products which result from reaction with diols, such as 1,3-propanediol, 1,4-butanediol, 1,6-hexanediol, diethylene glycol, neopentyl glycol, trimethyl-1,6-hexanediol, 3-methyl-1,5-pentanediol and/or tetraethylene glycol, with diaryl carbonates such as diphenyl carbonate, or with phosgene, as described in U.S. Pat. No. 4,533,729, DE-A-169 40 80, DE-A-271 43 03 or EP-B-0 343 572.

Usable polyether polyols include for example products which are accessible by polymerization of a cyclic oxide, for example ethylene oxide, propylene oxide or tetrahydrofuran or by addition of one or more of these oxides to polyfunctional initiators such as water, ethylene glycol, propylene glycol, diethylene glycol, cyclohexane dimethanol, glycerol, trimethylol propane, pentaerythrite or Bisphenol A. Particularly suitable polyether polyols are polyoxypropylene diols and triols, poly(oxyethylene-oxypropylene) diols and triols which are obtained by simultaneous or sequential addition of ethylene and propylene oxide to suitable initiators, as well as polytetramethylene ether glycols, which result from polymerization of tetrahydrofuran.

Suitable polyether polyols can also be obtained for example under the name "Desmophen" from Bayer, Leverkusen.

The polyester polyols are reaction products of low-molecular polyols with low-molecular polycarboxylic acids.

Low-molecular polyols or polyol mixtures suitable for this are for example ethylene glycol, propylene glycol, 1,4-butanediol, 1,6-hexanediol, diethylene glycol, triethylene glycol, neopentyl glycol, 1,4-bis(hydroxymethyl)-cyclohexane, dipropylene glycol. Glycerol, trimethylol propane or pentaerythrite are suitable for example as higher-functional polyols which can also be used proportionally, for example from 0 to 20 wt.-%, to introduce branchings into the polyester molecule. 1,6-hexane diol and neopentyl glycol are particularly suitable.

The low-molecular polycarboxylic acids can be for example aliphatic, cycloaliphatic, aromatic and/or heterocyclic. Instead of the free polycarboxylic acids, corresponding polycarboxylic acid anhydrides or polycarboxylic acid esters with low alcohols can also be used. As examples, there can be named: succinic acid, adipinic acid, sebacinic acid, azelaic acid, phthalic acid, isophthalic acid, phthalic acid anhydride, tetrahydrophthalic acid anhydride, glutaric acid anhydride, maleic acid, maleic acid anhydride, fumaric acid, terephthalic acid dimethyl ester. Adipinic acid is particularly preferred.

Suitable polyester polyols can also be obtained for example under the name "Desmophen" (Bayer, Leverkusen).

Polyesters which are accessible for example by polymerization of lactones, such as caprolactone, in conjunction with a polyol, can likewise be used. Polyester amide polyols can be obtained by proportional use of amino alcohols, such as ethanol amine, in the polyester-formation mixture.

Suitable polyolefin polyols are for example butadiene homo- and copolymers with terminal hydroxyl groups which can be obtained for example from BF Goodrich Speciality Chemicals, Cleveland, Ohio.

Commercially available urethane (meth)acrylates with a molecular weight greater than 1,200 g/mol are for example as follows, but the list does not claim to be complete and the invention is not to be understood as limiting in any way:

Urethan-MA 92-456, Urethan-A 98-446, Genomer 4269, Genomer 4215, Genomer 4246 (Rahn AG, Zurich), Ebecryl 230, Ebecryl 270, Ebecryl 930, (UCB Chemicals, Kerpen), BR-304, BR-374, BR-3731, BR-582E, BR-7432, BR-204 (Bomar Specialities Co., Winsted).

The urethane (meth)acrylate used according to the invention with the smaller molecular weight of component (f) can be for example a reaction product from a difunctional, for example aliphatic, cycloaliphatic and/or aromatic isocyanate, such as 1,6-hexamethylene diisocyanate (HDI), 2,4,4-trimethylhexamethylene-1,6-diisocyanate (TMDI), butyl isocyanate, tetramethylene diisocyanate, isophoron diisocyanate, 4,4'-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate, under amine or tin catalysis with a hydroxyalkyl and/or hydroxyaryl (meth)acrylate and/or di(meth)acrylate and/or tri(meth)acrylate such as 2-hydroxyethyl acrylate (HEA), 2-hydroxyethyl methacrylate (HEMA), 3-hydroxypropyl methacrylate (HPMA), 3-hydroxypropyl acrylate (HPA), glycerol dimethacrylate and/or glycerol diacrylate.

Usually, dental materials are formulated from the compositions according to the invention as two-component paste-paste systems in application systems or devices, such as cartridges from Mixpack, Rotkreuz.

The volume ratio of the pastes can be in the range from 1:1 to 20:1, preferably 4:1 to 10:1. The quantitatively larger component is hereafter called base paste, the smaller catalyst paste. However, the components can also be present distributed over three or more pastes. Single-component formulations are also possible with suitable choice of catalyst system.

The base paste can contain the total quantity of components (b) and (f), in addition optionally parts of quantities of components (c) and (d).

The catalyst paste optionally contains the residual or all quantities and/or constituents of components (c) and (d).

Component (e) can be contained in the base or catalyst paste or also distributed over both pastes. Component (a) is contained in the base paste or distributed over base and catalyst paste.

Mixing can be carried out by static or dynamic mixing processes. Manual admixing of the components is also possible, the components being stored for example in screw-top tubes or tubes, measured and mixed manually, for example by strand-length comparison.

A particularly preferred version within the framework of the invention is dosage as a two-component system with static mixing element.

A further preferred version of the invention relates to a kit for the preparation of a dental material containing either no or at least one application apparatus for the application of dental materials, no or at least one static mixing element, at least one cartridge with at least two chambers which are filled with a composition according to the invention.

The components are hereby distributed as follows for example:

Base paste: Component parts from (a), (b), parts from (c), parts from (e), (f)

Catalyst paste: Component parts from (a), parts from (c), (d), parts from (e).

Shaped bodies prepared according to the invention can have for example a bending strength, measured according to the 4-point bending test, of over 40 MPa, preferably from 70 to 150 MPa.

The fracture susceptibility of the shaped bodies according to the invention is for example maximum 40% with an endurance test of 100,000 loads of 100 N.

The invention is described in more detail in the following using examples, the invention not being limited in any way by the examples.

Preparation examples 100 g base and 10 g catalyst paste respectively are kneaded from the constituents listed hereafter of the preparation examples 1 to 5. Some of this is filled in 10:1 cartridges from Mixpack, Rotkreuz. For use, they are pressed by means of a dispenser through a static mixing device and mixed. Curing takes place within a few minutes.

| Component | Base 1 | Quantity g | wt.-% | Component | Catalyst 1 | Quantity g | wt.-% |
|---|---|---|---|---|---|---|---|
| a) | Dental glass powder (Ø < 12 μm), silanized with methacryloxypropyltrimethoxysilane | 25 | 25 | a) | Dental glass powder (Ø < 12 μm) | 3.4 | 34 |
| a) | Microfine silicic acid, silanized (HDKH 2000, Wacker, Burghausen) | 5 | 5 | a) | Microfine silicic acid, silanized (HDKH 2000, Wacker, Burghausen) | 0.7 | 7 |
| c) | Bis-(1-phenylpentane-1,3-dionato)-copper(II) | 0.00775 | 0.00775 | c) | 1-benzyl-5-phenyl barbituric acid | 0.1 | 1 |
| c) | (β-phenylethyl)-dibutyl-ammonium-chloride | 0.352 | 0.352 | c) | 3,5,5-trimethylhexanoic acid tertiary butyl ester | 0.06 | 0.6 |
| b) | 2,2-bis-4-(acryloxy-pentaethyleneglycol)-phenylpropane | 13.77 | 13.77 | d) | 2,2-bis-4-(2-hydroxyethoxyphenyl)-propane-bis-acetate | 5.74 | 57.4 |
| f) | Genomer 4215 (Rahn AG, Zurich) | 6.89 | 6.89 | | | | |
| f) | Genomer 4205 (Rahn AG, Zurich) | 48.98025 | 48.98025 | | | | |

| Component | Base 2 | Quantity g | wt.-% | Component | Catalyst 1 | Quantity g | wt.-% |
|---|---|---|---|---|---|---|---|
| a) | Dental glass powder (Ø < 12 μm), silanized with methacryloxypropyltrimethoxysilane | 25 | 25 | a) | Dental glass powder (Ø < 12 μm) | 3.4 | 34 |
| a) | Microfine silicic acid, silanized (HDKH 2000, Wacker, Burghausen) | 5 | 5 | a) | Microfine silicic acid, silanized (HDKH 2000, Wacker, Burghausen) | 0.7 | 7 |
| c) | Bis-(1-phenylpentane-1,3-dionato)-copper(II) | 0.00775 | 0.00775 | c) | 1-benzyl-5-phenyl barbituric acid | 0.1 | 1 |
| c) | (β-phenylethyl)-dibutyl-ammonium-chloride | 0.352 | 0.352 | c) | 3,5,5-trimethylhexanoic acid tertiary butyl ester | 0.06 | 0.6 |
| b) | TEGDMA | 13.77 | 13.77 | d) | 2,2-bis-4-(2-hydroxyethoxyphenyl)-propane-bis-acetate | 5.74 | 57.4 |
| f) | U 98-446 (Rahn AG, Zurich) | 13.77 | 13.77 | | | | |
| f) | Genomer 4205 (Rahn AG, Zurich | 42.10025 | 42.10025 | | | | |

| Component | Base 3 | Quantity g | wt.-% | Component | Catalyst 1 | Quantity g | wt.-% |
|---|---|---|---|---|---|---|---|
| a) | Dental glass powder (Ø < 12 μm), silanized with methacryloxypropyltrimethoxysilane | 25 | 25 | a) | Dental glass powder (Ø < 12 μm) | 3.4 | 34 |
| a) | Microfine silicic acid, silanized (HDKH 2000, Wacker, Burghausen) | 5 | 5 | a) | Microfine silicic acid, silanized (HDKH 2000, Wacker, Burghausen) | 0.7 | 7 |
| c) | Bis-(1-phenylpentane-1,3-dionato)-copper(II) | 0.00775 | 0.00775 | c) | 1-benzyl-5-phenyl barbituric acid | 0.1 | 1 |
| c) | (β-phenylethyl)-dibutyl-ammonium-chloride | 0.352 | 0.352 | c) | 3,5,5-trimethylhexanoic acid tertiary butyl ester | 0.06 | 0.6 |
| b) | TEGDMA | 10.33 | 10.33 | d) | 2,2-bis-4-(2-hydroxyethoxyphenyl)-propane-bis-acetate | 5.74 | 57.4 |
| f) | Ebecryl 230 (UCB, Kerpen) | 10.33 | 10.33 | | | | |
| f) | 7,7,9-trimethyl-4, 13-dioxo-3, 14-dioxa-5, 12-diazahexadecane-1, 16-dioxy-dimethacrylate | 48.98025 | 48.98025 | | | | |

| Component | Base 4 | Quantity g | wt.-% | Component | Catalyst 1 | Quantity g | wt.-% |
|---|---|---|---|---|---|---|---|
| a) | Dental glass powder (Ø < 3 μm), silanized with methacryloxypropyltrimethoxysilane | 25 | 25 | a) | Dental glass powder (Ø < 12 μm) | 3.4 | 34 |
| a) | Microfine silicic acid, silanized (HDKH 2000, Wacker, Burghausen) | 5 | 5 | a) | Microfine silicic acid, silanized (HDKH 2000, Wacker, Burghausen) | 0.7 | 7 |
| c) | Bis-(1-phenylpentane-1,3-dionato)-copper(II) | 0.00775 | 0.00775 | c) | 1-benzyl-5-phenyl barbituric acid | 0.1 | 1 |
| c) | (β-phenylethyl)-dibutyl-ammonium-chloride | 0.352 | 0.352 | c) | 3,5,5-trimethylhexanoic acid tertiary butyl ester | 0.06 | 0.6 |
| b) | 2,2-bis-4-(acryloxy-pentaethyleneglycol)-phenylpropane | 13.77 | 13.77 | d) | 2,2-bis-4-(2-hydroxyethoxyphenyl)-propane-bis-acetate | 5.74 | 57.4 |
| f) | U 98-446 (Rahn AG, Zurich) | 6.89 | 6.89 | | | | |
| f) | 7,7,9-trimethyl-4, 13-dioxo-3, 14-dioxa-5, 12-diazahexadecane-1, 16-dioxy-dimethacrylate | 48.98025 | 48.98025 | | | | |

| Component | Base 5 | Quantity g | wt.-% | Component | Catalyst 1 | Quantity g | wt.-% |
|---|---|---|---|---|---|---|---|
| a) | Dental glass powder (Ø < 1 μm), silanized with methacryloxypropyltrimethoxysilane | 25 | 25 | a) | Dental glass powder (Ø < 1 μm) | 3.4 | 34 |
| a) | Microfine silicic acid, silanized (HDKH 2000, Wacker, Burghausen) | 5 | 5 | a) | Microfine silicic acid, silanized (HDKH 2000, Wacker, Burghausen) | 0.7 | 7 |
| c) | Bis-(1-phenylpentane-1,3-dionato)-copper(II) | 0.00775 | 0.00775 | c) | 1-benzyl-5-phenyl barbituric acid | 0.1 | 1 |
| c) | (β-phenylethyl)-dibutyl-ammonium-chloride | 0.352 | 0.352 | c) | 3,5,5-trimethylhexanoic acid tertiary butyl ester | 0.06 | 0.6 |
| b) | 2,2-bis-4-(acryloxy-pentaethyleneglycol)-phenylpropane | 13.77 | 13.77 | d) | 2,2-bis-4-(2-hydroxyethoxyphenyl)-propane-bis-acetate | 5.74 | 57.4 |
| f) | Ebecryl 270 (UCB, Kerpen) | 10.33 | 10.33 | | | | |
| f) | 7,7,9-trimethyl-4, 13-dioxo-3, 14-dioxa-5, 12-diazahexadecane-1, 16-dioxy-dimethacrylate | 45.54025 | 45.54025 | | | | |

Ø: diameter

Testpieces with dimensions 4 mm*4 mm*35 mm were prepared and, in an endurance test, loaded 100,000 times with 100 N in water at 36° C. in the 4-point bending test according to FIG. 1 (one load per second, support at a distance of 30 mm, load at a distance of 15 mm, maximum possible deformation of the sample pieces of 1.4 mm determined by the apparatus).

The results obtained are summarized in the following table:

| Dental material | Bending strength [MPa] 4-point bending test | Endurance test 100,000 loads of 100 N |
| --- | --- | --- |
| Comparative example 1: TRIM (Bosworth, Illinois) | 40 | 100% of the testpieces permanently deformed after less than 10,000 loads |
| Comparative example 2: Flexspan (Jeneric/Pentron, Wallingford) | 70 | 100% of testpieces broken |
| Comparative example 3: Luxatemp Automix (DMG, Hamburg) | 85 | 75% of testpieces broken |
| Preparation example 1 (according to the invention) | 60 | 25% of testpieces broken |
| Preparation example 2 (according to the invention) | 50 | 35% of testpieces broken |
| Preparation example 3 (according to the invention) | 50 | 40% of testpieces broken |
| Preparation example 4 (according to the invention) | 70 | 25% of testpieces broken |
| Preparation example 5 (according to the invention) | 60 | 30% of testpieces broken |

The dental materials according to the invention, according to preparation examples 1 to 5, show a clearly reduced fracture susceptibility and/or improved dimensional stability vis-à-vis conventional materials. The dental materials according to the invention have a bending strength sufficient for provisional K+B materials in addition to low fracture susceptibility.

What is claimed is:

1. A composition comprising:
   (a) 15 to 60 wt.-% fillers,
   (b) 3 to 35 wt.-% of at least one mono- or polyethylenically unsaturated compound which is not a urethane (meth)acrylate and has a molecular weight between 300 and 5,000 g/mol,
   (c) 0.1 to 5 wt.-% of at least one initiator system which is capable of starting a radical reaction,
   (d) 1 to 40 wt.-% plasticizers,
   (e) 0 to 10 wt.-% auxiliaries, and
   (f) 30 to 81.9 wt.-% of at least two urethane (meth)acrylates with different molecular weights, a high molecular weight urethane (meth)acrylate having a molecular weight between 1,000 and 20,000 g/mol and a low molecular weight urethane (meth)acrylate having a molecular weight between 300 and 1,000 g/mol, being present in a molecular weight ratio of 1.5:1 to 50:1.

2. The composition according to claim 1, in which the urethane (meth)acrylates of component (f) constitute at least 50 wt.-% of the total weight of the ethylenically unsaturated compounds (b) and (f).

3. The composition according to claim 1 or 2, the high-molecular weight urethane (meth)acrylate being selected from the group consisting of polyether (meth)acrylates, polyester (meth)acrylates and polycarbonate urethane oligomer (meth)acrylates.

4. The composition according to claim 1 or 2, component (b) being an acrylic acid ester and/or a methacrylic acid ester of at least one compound selected from the group consisting of an ethoxylated compound, a propoxylated compound, a polyether and an alkylpolyol.

5. The composition according to claim 1 or 2, in which component (d) has a viscosity smaller than 10 Pa·s at 23° C.

6. The composition according to claim 1 or 2, in which component (d) has a molecular weight between 150 g/mol and 5,000 g/mol.

7. The composition according to claim 1 or 2 that is in the form of a system of at least two pastes able to be admixed in customary dental application systems.

8. The composition according to claim 1 or 2 that is formulated as a single-component system.

9.

10. A kit for the preparation of a dental material, comprising at least one cartridge with at least two chambers which are filled with a composition according to claim 1 or 2 and optionally comprising at least one apparatus for applying a dental material and further optionally comprising at least one static mixing element.

11. A cured composition according to claim 1 or 2.

12. An apparatus comprising at least one cartridge containing a composition according to claim 1 or 2.

13. The composition of claim 1, in which the auxiliaries are at least one selected from the group consisting of dyes, pigments, stabilizers, solvents and rheological additives.

14. The composition of claim 13 in which the auxiliaries are at least one rheological additive that is a flow-improver or a flow retarder.

15. A method for preparing a dental piece selected from the group consisting of a provisional crown, a dental bridge, a dental filling, a dental inlay and a dental onlay comprising forming the composition of claim 1 or 2 into the dental piece and curing the composition.

16. A method for preparing a dental material with a fracture susceptibility of maximum 40% in an endurance test of 100,000 loads of 100 N comprising:
   i) providing a composition comprising
      (a) 15 to 60 wt.-% fillers,
      (b) 3 to 35 wt.-% of at least one mono- or polyethylenically unsaturated compound which is not a urethane (meth)acrylate and has a molecular weight between 300 and 5,000 g/mol,
      (c) 0.1 to 5 wt.-% of at least one initiator system which is capable of starting a radical reaction,
      (d) 1 to 40 wt.-% plasticizers,
      (e) 0 to 10 wt.-% auxiliaries, and
      (f) 30 to 81.9 wt.-% of at least two urethane (meth)acrylates with different molecular weights, a high molecular weight urethane (meth)acrylate having a molecular weight between 1,000 and 20,000 g/mol and a low molecular weight urethane (meth)acrylate having a molecular weight between 300 and 1,000 g/mole, being present in a molecular weight ratio of 1.5:1 to 50:1; and
   ii) curing the composition.

17. The method of claim 16, in which the auxiliaries are at least one selected from the group consisting of dyes, pigments, stabilizers, solvents and rheological additives.

18. The method of claim 17, in which the auxiliaries are at least one rheological additive that is a flow-improver or a flow retarder.

19. A method for preparing a dental material with a bending strength, measured according to the 4-point bending test, of over 40 MPa comprising:
  i) providing a composition comprising
    (a) 15 to 60 wt.-% fillers,
    (b) 3 to 35 wt.-% of at least one mono- or polyethylenically unsaturated compound which is not a urethane (meth)acrylate and has a molecular weight between 300 and 5,000 g/mol,
    (c) 0.1 to 5 wt.-% of at least one initiator system which is capable of starting a radical reaction,
    (d) 1 to 40 wt.-% plasticizers,
    (e) 0 to 10 wt.-% auxiliaries, and
    (f) 30 to 81.9 wt.-% of at least two urethane (meth)acrylates with different molecular weights, a high molecular weight urethane (meth)acrylate having a molecular weight between 1,000 and 20,000 g/mol and a low molecular weight urethane (meth)acrylate having a molecular weight between 300 and 1,000 g/mole, being present in a molecular weight ratio of 1.5:1 to 50:1; and
  ii) curing the composition.

20. The method of claim 19, in which the auxiliaries are at least one selected from the group consisting of dyes, pigments, stabilizers, solvents and rheological additives.

21. The method of claim 20, in which the auxiliaries are at least one rheological additive that is a flow-improvers or flow retarder.

* * * * *

UNITED STATES PATENT AND TRADEMARK OFFICE
CERTIFICATE OF CORRECTION

PATENT NO. : 6,936,642 B2  Page 1 of 1
APPLICATION NO. : 10/168092
DATED : August 30, 2005
INVENTOR(S) : Thomas Lehmann It is certified that error appears in the above-identified patent and that said Letters Patent is hereby corrected as shown below:

<u>On the Title Page, Item (86), under (Filing Date)</u>
Line 1, after "Date:" delete "Oct. 3, 2002" and insert -- Oct. 31, 2002 --, therefor.

<u>Column 1</u>
Line 4, delete "PCT/EPOO/" and insert -- PCT/EP00/ --, therefor.

<u>Column 3</u>
Line 51, delete "Di(meth)acrylates" and insert -- di(meth)acrylates --, therefor.
Line 60, delete "Di(meth)acrylates" and insert -- di(meth)acrylates --, therefor.

<u>Column 12</u>
Line 32, after "13" insert -- , --.

Signed and Sealed this

Thirteenth Day of May, 2008

JON W. DUDAS
*Director of the United States Patent and Trademark Office*